United States Patent [19]

Hoefer et al.

[11] 4,325,796
[45] Apr. 20, 1982

[54] VERTICAL GEL SLAB ELECTROPHORESIS APPARATUS AND METHOD THEREFOR

[75] Inventors: Peter S. Hoefer, San Francisco; Michael G. Whitesides, Daly City, both of Calif.

[73] Assignee: Hoefer Scientific Instruments, San Francisco, Calif.

[21] Appl. No.: 229,957

[22] Filed: Jan. 30, 1981

Related U.S. Application Data

[60] Continuation-in-part of Ser. No. 121,288, Feb. 13, 1980, Pat. No. 4,290,871, which is a division of Ser. No. 714, Jan. 3, 1979, Pat. No. 4,224,134.

[51] Int. Cl.³ .................. B01D 57/02; G01N 27/26
[52] U.S. Cl. ........................ 204/180 G; 204/299 R
[58] Field of Search .................. 204/180 G, 299 R; 23/230 B; 429/12

[56] References Cited

U.S. PATENT DOCUMENTS

| | | | |
|---|---|---|---|
| 3,980,540 | 9/1976 | Hoefer | 204/180 G |
| 4,035,377 | 7/1977 | Detroy | 204/180 G X |
| 4,169,036 | 9/1979 | Anderson et al. | 204/180 G X |

Primary Examiner—Howard S. Williams
Attorney, Agent, or Firm—Flehr, Hohbach, Test, Albritton & Herbert

[57] ABSTRACT

A vertical gel slab electrophoresis apparatus includes a pair of sample units (12, 13) each of which is a pair of clamped together, spaced glass plates (23a, 23b and 24a, 24b) for containing the gel (21, 22). A casting stand is provided which holds the pair of sample units vertical and seals their bottom slots (26, 27) to prevent leakage of the gel. After polymerization, an upper buffer solution container (33) is locked on to the pair of sample units, the casting stand removed, and the remaining U-shaped structure placed in a tank (11) where electrophoresis may be initiated.

A specialized seal is provided between the sample units and the upper buffer chamber (33) in the form of a resilient gasket (36, 37) stretched over the one end of a pair of sample plates and this is then wedged into a mated truncated conical sleeve extending from the bottom (34) of the upper buffer container to provide a seal which effectively isolates the upper buffer solution (32) from the lower buffer solution (28).

8 Claims, 12 Drawing Figures

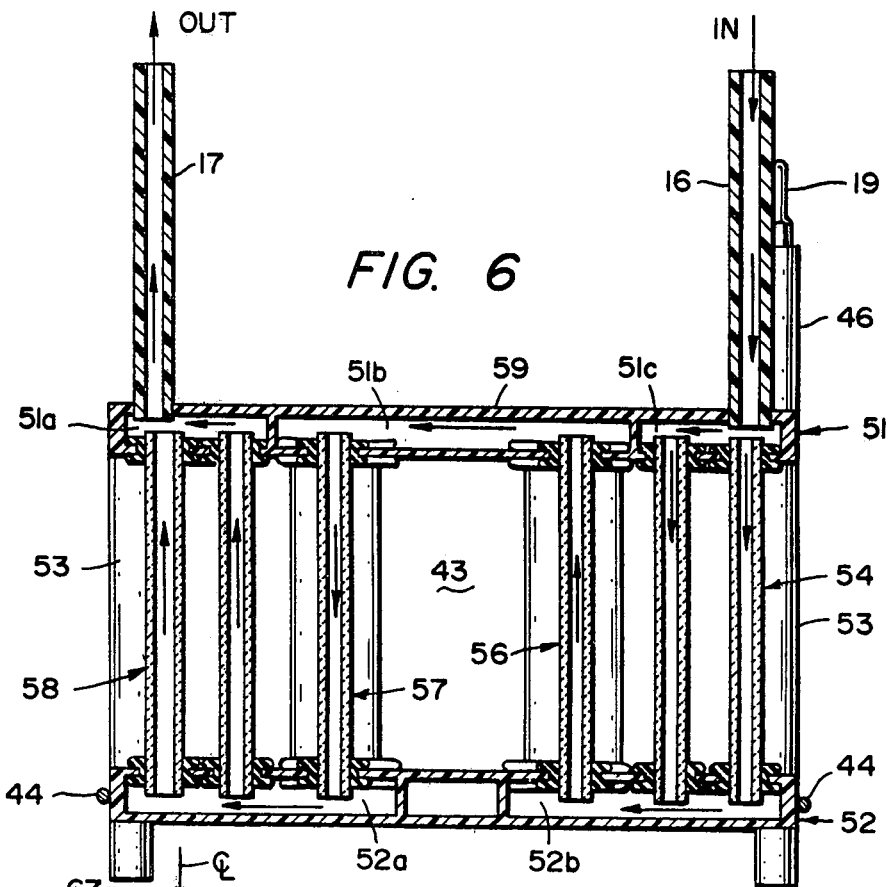
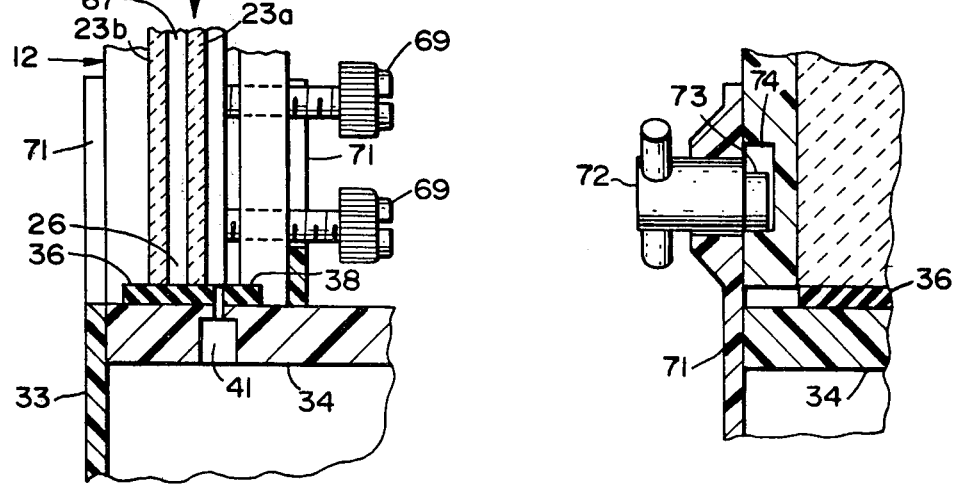
FIG. 6
FIG. 4
FIG. 5

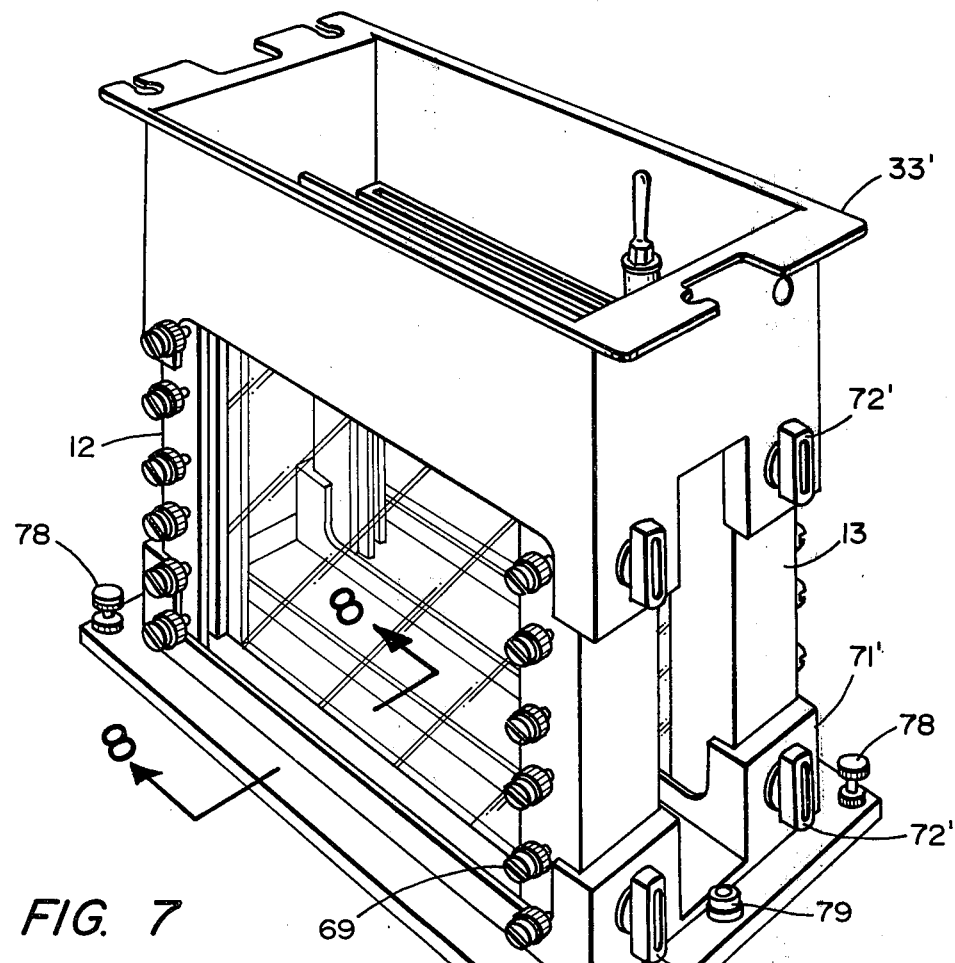
FIG. 7
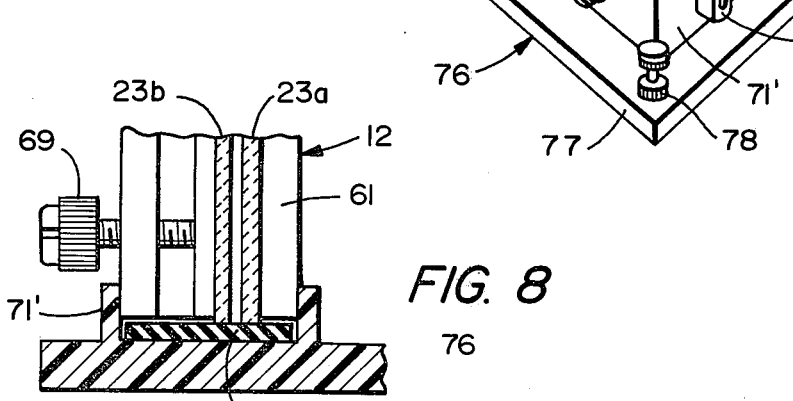
FIG. 8
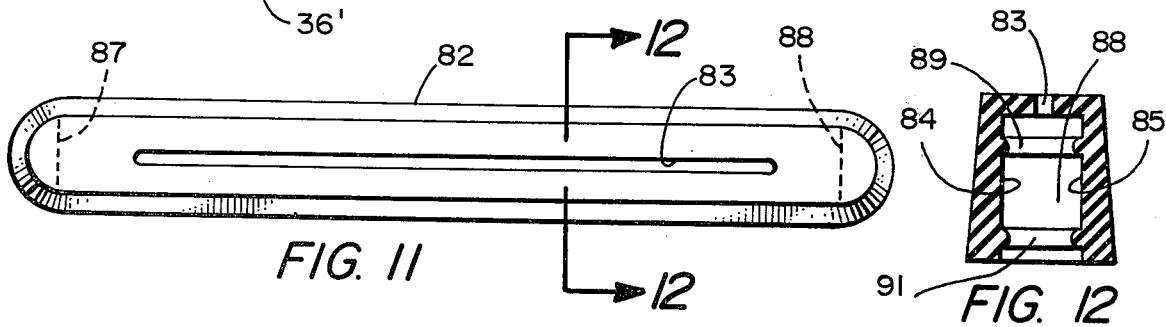
FIG. 11
FIG. 12

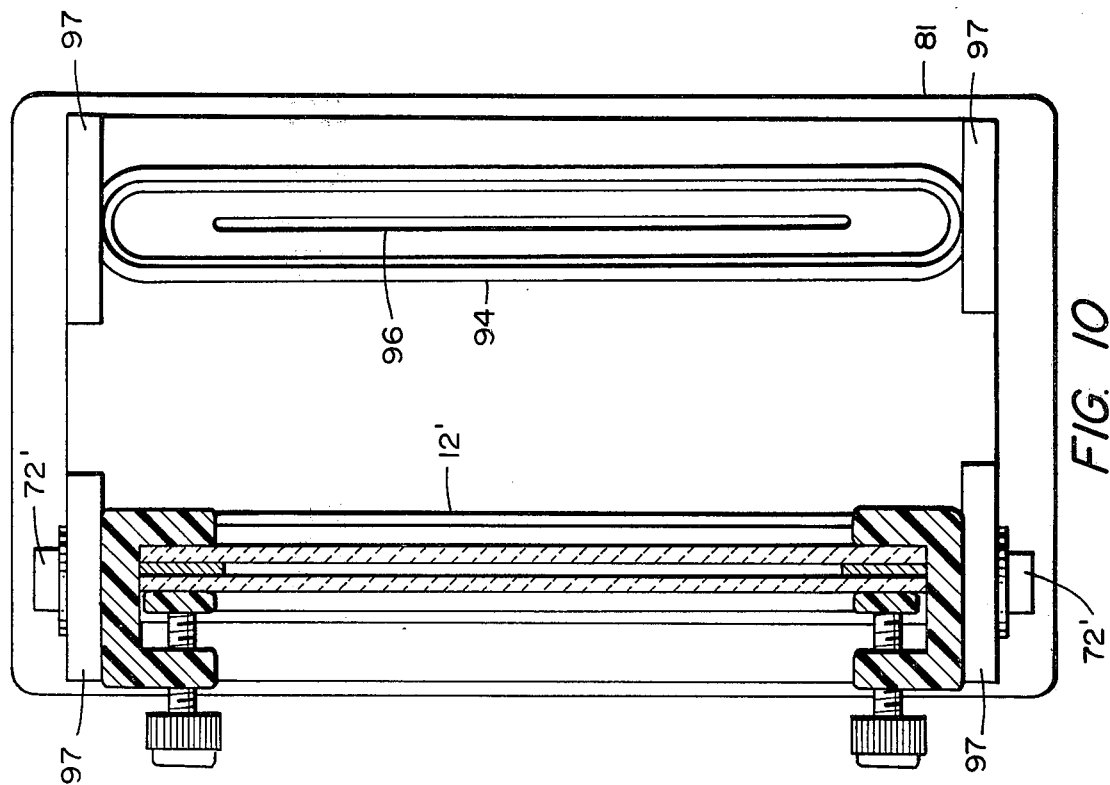
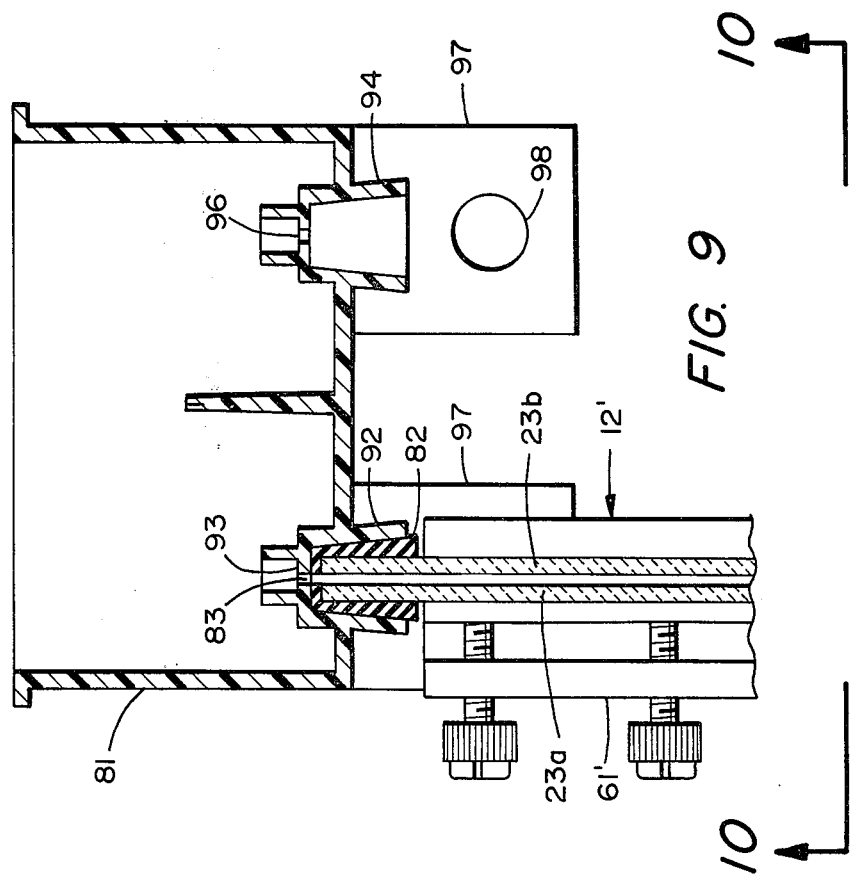

VERTICAL GEL SLAB ELECTROPHORESIS APPARATUS AND METHOD THEREFOR

This is a Continuation-In-Part of application Ser. No. 121,288, filed Feb. 13, 1980, now U.S. Pat. No. 4,290,871, which is a division of application Ser. No. 000,714, filed Jan. 3, 1979, now U.S. Pat. No. 4,224,134, issued Sept. 23, 1980.

The present invention is directed to a vertical gel slab electrophoresis apparatus and method therefor.

When carrying out the process of gel electrophoresis, it is necessary to first fill the sample unit with gel and secondly apply an appropriate voltage to cause electrophoretic separation of the sample within the gel slab.

To accomplish the above, application of a voltage to upper and lower conductive buffer solutions which respectively contact both end slots of the sample unit is necessary. These buffer solutions, because of the potential between them, are separated into isolated compartments by several different techniques. One is illustrated in U.S. Pat. No. 3,980,540 in the name of Stanton A. Hoefer, assigned to the present assignees. In this foregoing patent, the first step of filling the sample unit is conducted by placing a rubber seal against the bottom slot of the sample unit and then injecting gel through the bottom seal by means of a hypodermic needle. The seal is then removed from the bottom of the plate by a camming arrangement where the plate remains stationary and the seal itself is lowered in order to expose the bottom slot to a buffer solution.

The foregoing two-step process of first filling the sample unit with gel and secondly, with the use of a buffer solution, supplying the voltage across the sample unit and the concomitant required electrical isolation of the buffer solution, can lead to complex apparatus or operational set-ups for which simplification is always desirable from an operator's standpoint.

It is therefore an object of the present invention to provide an improved vertical gel slab electrophoresis apparatus and method therefor.

In accordance with the above object there is provided such apparatus which comprises a pair of sample units each including a pair of clamped together spaced plates for containing gel and with open top and bottom slots. Casting stand means hold the pair of sample units vertical and seal the bottom slots to prevent leakage of the gel. Upper buffer solution container means have a pair of apertures sealed against and mated with the top slots of said sample units to provide liquid communication with an upper buffer solution, and includes means for sealing the top slots and for retaining the sample units with the upper container, whereby the casting stand may be removed from the sample units after the gel is polymerized.

There is also provided a vertical gel slab electrophoresis method using a pair of sample units each including a pair of clamped together spaced plates for containing gel and with open top and bottom slots and including a casting stand for holding said units vertical, and an upper buffer solution container having a pair of apertures, the method comprising the steps of locking said sample units in the stand in a vertical position to seal the bottom slots to prevent leakage of gel. At least one sample unit is filled with gel and polymerized. The upper buffer solution container is locked to the sample units and the upper slots sealed against the apertures to provide liquid communication with an upper buffer solution. The casting stand-container combination is unlocked and removed from the sample units whereby electrophoresis may be accomplished.

From a more detailed aspect, there is provided vertical gel slab electrophoresis apparatus comprising an upper buffer container including at least one elongated aperture with a truncated conical sleeve centered thereon and extending downwardly therefrom. A sample unit includes a pair of clamped together spaced plates for containing gel and with open top and bottom slots. An elongated resilient gasket having a truncated conical cross-section mates with the sleeve, is stretched over the pair of plates and the top slot. Means are provided for wedging the gasket into the sleeve to provide a liquid seal.

FIG. 4 is an enlarged cross-sectional view taken along the line 4—4 of FIG. 3;

FIG. 5 is an enlarged cross-sectional view taken substantially along the line 5—5 of FIG. 3;

FIG. 6 is a cross-sectional view of a heat exchanger portion of FIG. 2;

FIG. 7 is a perspective view illustrating the invention;

FIG. 8 is a fragmentary cross-sectional view taken along the line 8—8 of FIG. 7;

FIG. 9 is a fragmentary and simplified cross-sectional view of an alternative embodiment but corresponding to a cross-sectional side elevation of FIG. 7;

FIG. 10 is a bottom view of FIG. 9 taken along the line 10—10;

FIG. 11 is a plane view of a component of FIG. 9; and

FIG. 12 is a cross-sectional view taken along the line 12—12 of FIG. 11.

Figure 1:
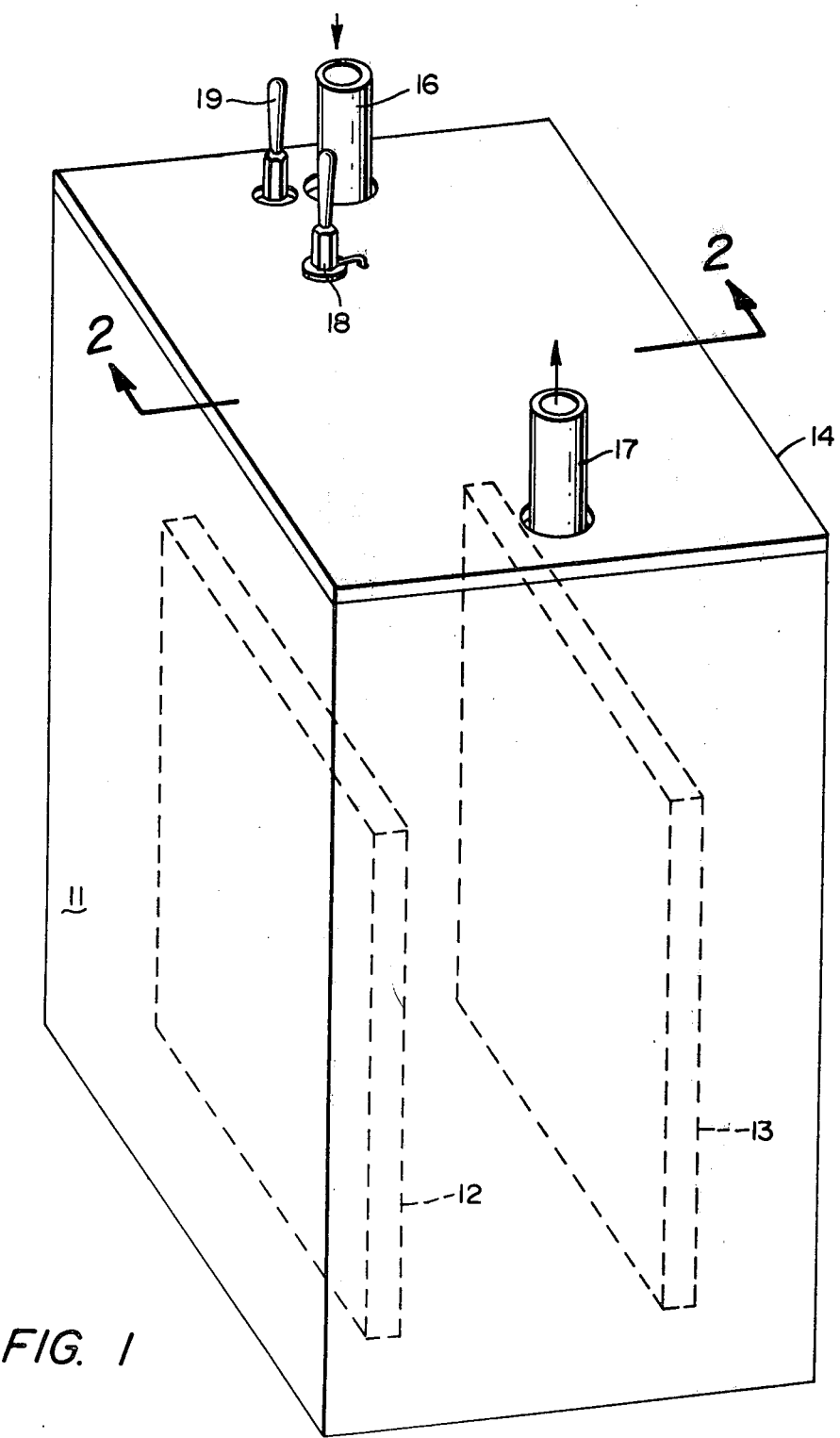
FIG. 1 is a perspective view of a slab electrophoresis unit embodying the present invention.

FIG. 1 illustrates the overall vertical gel slab electrophoresis unit of the present invention. It includes a lower buffer solution tank or container 11 holding a pair of sample units 12 and 13 containing gel which are shown in dashed-outline and will be described in detail below. Container 11 has a top 14 having two apertures for the heat exchanger or coolant tubes 16 and 17. In addition, means for applying an electrical voltage across the buffer solutions to produce the electrophoresis effect consists of one terminal 18 mounted on top 14 and a second terminal 19 extending through an aperture in the top.

In general, in the casting mode gel is polymerized along with the formation of suitable sample wells, in sample units 12 and 13. Then in the operating mode a voltage is applied across terminals 18 and 19 to place an electric field across the top and bottom of the respective sample units 12 and 13 to cause electrophoretic separation.

Figure 2:
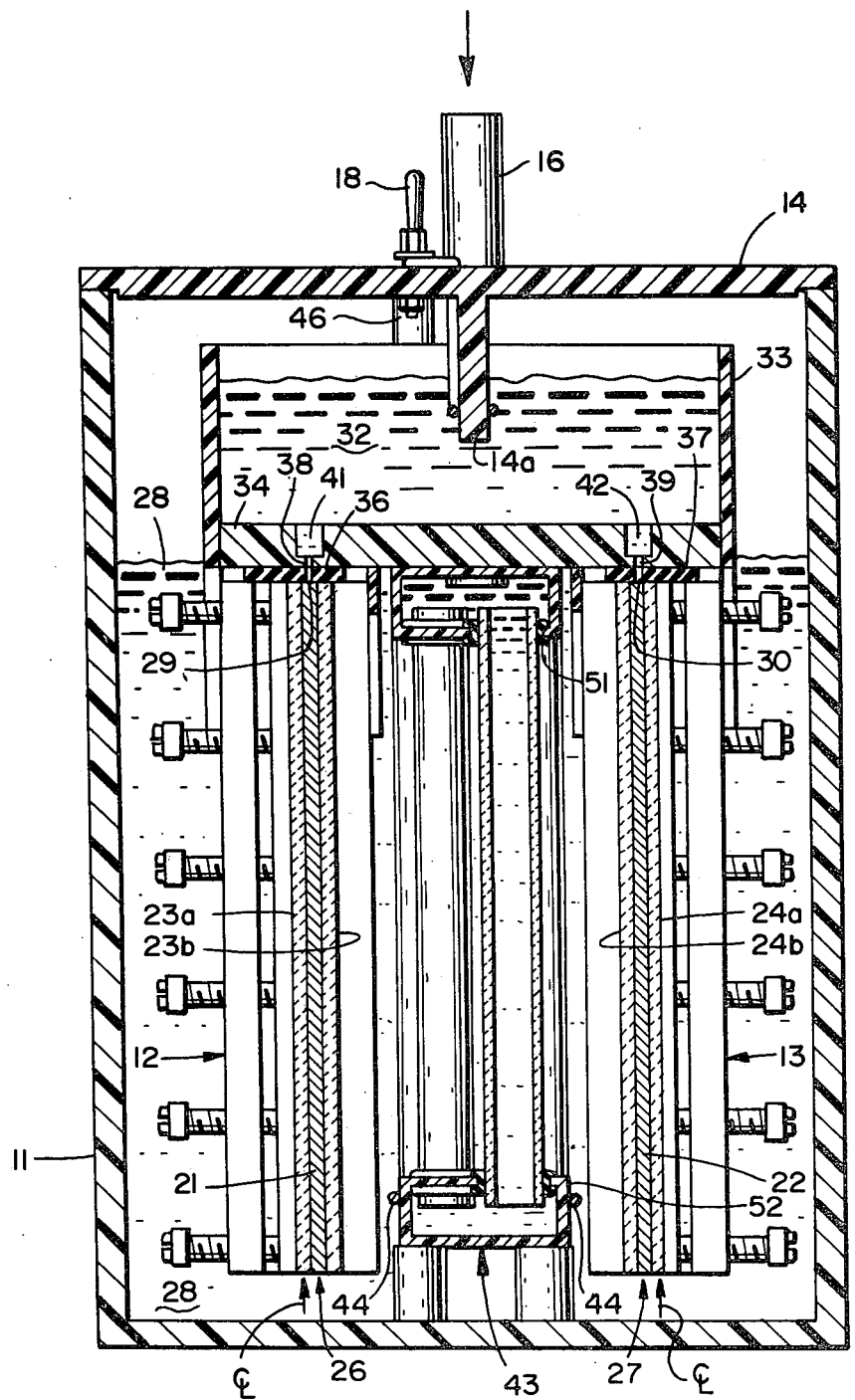
FIG. 2 is a detailed cross-sectional view taken along the line 2—2 of FIG. 1.

FIG. 2 best illustrates this operational mode, the cross-section of FIG. 1 illustrating the sample units 12 and 13 which contain polymerized gel 21, 22, respectively, between pairs of spaced rectangular glass plates 23a, 23b and 24a, 24b. Each pair of plates 23, 24 has a bottom slot 26,27 which makes liquid contact with the conductive buffer solution 28, in partially filled tank 11 and a top slot 29 and 30 which are in liquid communication with conductive upper buffer solution 32 which is in the container 33.

More specifically, the bottom 34 of container 33 has fastened to it a pair 36, 37 of longitudinal sealing strips constructed of resilient material each of which has an elongated aperture 38, 39 which as illustrated in FIG. 2 mate with the slots 29 and 30.

Apertures 38, 39 lead through into the container 33 by means of apertures 41 and 42 in bottom 34. The top portion of apertures 41 and 42 are enlarged so that two-dimensional electrophoresis may be carried on by laying a tube gel in the enlarged portion. This is of course done with the top 14 off and no upper buffer liquid 32 in place. It is obvious that there is ample room to insert the tube gel.

Upper buffer solution 32 makes electrical contact with terminal 18 through top 14 which on its extension 14a carries an electrode, connected to terminal 18, which would be normally immersed in the buffer solution 32.

It is apparent (and also referring to FIG. 3 briefly) container 33 and its downwardly extending sample units 12 and 13 form a U-shaped structure of which the container is the upper bight portion and the sample units 12 and 13 are the legs of the U. The bight portion, by way of its bottom 34, is supported by the heat exchanger or cooling unit 43 which is illustrated in greater detail or better perspective in FIG. 6. Heat exchanger 43 has on its lower portion a loop conductor 44 which makes electrical contact with the lower buffer solution 28 and is electrically connected to terminal 19 by a convenient vertical support post extension 46 of the heat exchanger unit 43. (See FIG. 6 again.)

Heat exchanger 43 as shown in greater detail in FIG. 6 in fact provides a serpentine path in a vertical plane for the cooling liquid as it travels from the input 16 to the output 17. That is provided by combination of a top manifold 51 and a bottom manifold 52 which are held together by vertical posts 53. Top manifold 51 has three compartments 51a, 51b and 51c. Bottom manifold 52 has compartments 52a and 52b. A center aperture can be used for a magnetic stirrer if desired. To provide for the cooling effect clusters of three tubes 54 connect manifold portion 51c to 52b. Tube cluster 56 connects 52b to 51b. Cluster 57 connects 51b to 52a. And lastly, three-tube cluster 58 connects manifold 52a to 51a and thence to the outlet tube 17. By the use of a serpentine path and the cluster of three tubes a large cooling area is provided for the lower buffer solution 28. Referring to FIG. 2 it is also apparent that the lower buffer solution is in full contact with both plates 23a, 23b and 24a, 24b so that effective cooling or temperature regulation is provided for both sides of each sample unit.

As discussed before, the U-shaped structure of FIG. 2 formed by container unit 33 and the sample units 12 and 13 rests on the top surface 59 of manifold 51 between an outlet tube 16 and 17. Thus the length of the sample units in a vertical direction can be increased merely by lengthening the support ports 53 of the heat exchanger 43 (and of course also deepening the tank 11).

Figure 3:
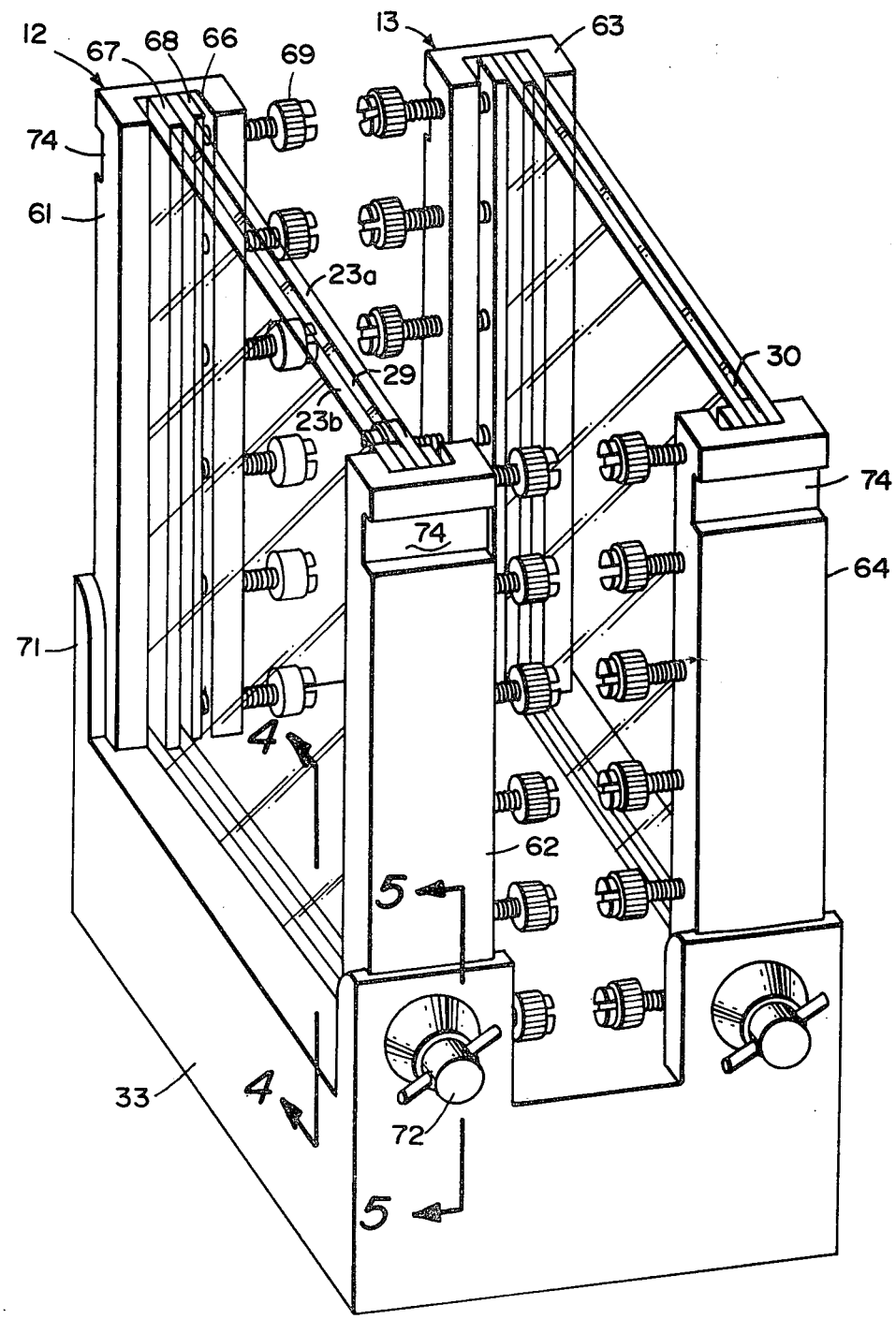
FIG. 3 is a perspective view of an interior portion of FIGS. 1 and 2 which has been flipped.

FIG. 3 illustrates the U-shaped structure of FIG. 2 removed from the tank 11 and inverted. Thus container 33 now serves as the base for sample units 12 and 13. This is done during the casting mode where the gel is placed through the open top slot 29 in the case of sample unit 12, and 30 in the case of sample unit 13. It is therefore apparent that the orientation of sample units 12 and 13 in this casting mode have been shifted and that both units have in essence been rotated about their horizontal axis 180°. In other words, referring to FIG. 4, slot 26 is now against the sealing strip 36 whereas in FIG. 2 it was exposed to buffer solution 28. In the casting mode when the gel is placed in the sample unit the bottom of the sample unit must of course be sealed. Thereafter when the gel is polymerized the seal can be removed in the operational mode proceeded with where both ends of the gel are exposed to a voltage difference to provide for the electrophoresis. However, in accordance with the invention the sealed casting mode is provided by reason of the fact that by changing orientation of the sample units 12 and 13 (i.e. flipping) and the fact that the sample units have a centerline from which the pair of plates 23a, 23b and 24a, 24b are offset. This allows the sample units to be filled as illustrated in FIGS. 3 and 4, the sample units removed, either flipped or rotated along the vertical axis by 180° and reinserted to retake the position shown in FIG. 2. This is of course where the slots 29 and 30 mate with apertures 38 and 39 of the bottom 34 of the upper buffer solution container 33.

If no sample wells are desired but rather a two-dimensional electrophoresis carried on by the use of enlarged portions 41 and 42 of the bottom 34 of tank 33 as illustrated in FIG. 2, then of course the sample units need only be rotated along their vertical axis by 180° since no comb type well forming structure need be used.

Although not illustrated specifically in FIG. 3 a common technique in the casting mode is to provide a comblike plastic structure which would be inserted in the slots 29 and 30 during the polymerization of the gel so as to form a number of vertical sample wells. Thereafter in order to position these sample wells with the appropriate apertures in the upper buffer solution tank 33, sample units 12 and 13 must be flipped about their horizontal axis. This is quite apparent where the retaining screws for the sample plates in FIG. 2 are outwardly pointing and in FIG. 3 inwardly pointing.

Now referring to the detailed construction of the sample units which is also illustrated in FIGS. 4 and 5, each sample unit includes a pair of vertical guides 61, 62 in the case of unit 12, and 63, 64 in the case of unit 13. Each guide has an internal groove, for example 66 in the case of guide 61, in which is located in sequence a glass plate 23b, a spacer 67 which determines the thickness of the gel, glass plate 23a and a final spacer 68 against which a screw 69 presses. Thus, referring to FIG. 4 where the centerline is indicated coinciding with plate 23a, the offset nature of the glass plates is quite apparent. And of course this lateral offset allows for the changing orientation of the sample units to provide both a casting mode and an operational mode with basically the same common structure.

Sample units 12 and 13 (referring again to FIG. 3 and now FIG. 5) are held into place by the channels 71 extending from container 33 illustrated in FIG. 5. At the end of the channel 71 is a cam unit 72 which has an off-center nub 73 which mates with a horizontal channel 74 which is located at the upper and lower portion of each guide rail 61, 62, 63 and 64. As illustrated in FIGS. 4 and 5 when the cam 72 is rotated in one direction or the other it will press the pair of glass plates onto the sealing strip 36.

FIG. 7 illustrates an alternative technique in the casting step (where gel is placed in the sample units and then polymerized) which eliminates the flipping or changing the orientation of the sample units 12 and 13. What is done here comparing FIG. 7 to FIG. 3, is that rather than using the upper buffer container 33, a simplified casting stand 76 is utilized which still includes the channels 71 into which the sample units 12 and 13 fit and equivalent camming units 72'. Rather than having a container portion of 33, however, the structure rests on a flat base 77 which includes leveling screws 78 and a level 79. However, one difference is, as illustrated in FIG. 8, is that the sealing strip 36' in comparison to the sealing strip 36 of FIG. 4 is solid rather than having a slit in it since it is only used for this casting purpose. With respect to sealing, it should be noted that the ends of the glass plates 23a, 23b extend approximately 0.5 of a millimeter past the ends of the clamping unit or guide 61 of the sample unit 12.

And referring again to FIG. 7 since there is no need to change the orientation of the plates or flip them, therefore the screws 69 on the plates are facing outwardly (as opposed to inwardly as illustrated in FIG. 3 in the casting mode) thus making the sample units ready to be mated with the upper buffer chamber 33' and placed in the electrophoresis container in the manner illustrated in FIG. 2. Container 33' is similar to container 33 and differs in ornamental appearance and superficial structure only. It also includes the cam units 72' which interact with the horizontal grooves 74 (see FIG. 3) in the sample units providing for a locking of one to the other.

Thus in summary and referring to FIGS. 7 and 8 from a method standpoint, the sample units 12 and 13 after being clamped together or assembled in the proper manner are placed in the casting stand 76 as illustrated. The four cam units 72' are rotated to lock the sample units in the stand in a vertical position and to also seal the bottom slots of the sample unit against the sealing strip 36' (FIG. 8) preventing a leakage of the liquid gel which is subsequently added through the open top slots of the sample units.

Next the gel is polymerized. During this step of course heat may be generated and if desired, the unit thus far assembled, i.e. the casting stand 76 and sample units 12 and 13 filled with gel, may be placed in the tank 11 (FIG. 1) and cooled with the cooling unit of FIG. 6 which is placed in the U-shaped hollow formed by the casting stand and sample units. Thus in this very critical polymerization step uniform cooling is provided.

Next the upper buffer container 33' is placed over the sample units 12 and 13 and locked by the use of cams 72' to form the U-shaped casting stand-container combination illustrated in FIG. 2; that is, the combination of the upper buffer container unit 33 and the sample units 12 and 13.

Removal of the casting stand 76 by unlocking the cam units 72' allows the U-shaped casting stand-container combination to be removed and placed in the tank 11 as illustrated in FIG. 2 where electrophoresis may be accomplished.

Now referring to FIGS. 9–12, they represent an alternative method of sealing the sample units against the upper buffer container, and specifically the longitudinal resilient sealing means itself. In FIG. 2 this is shown as the flat strips 36 which are slit. In contrast as illustrated in FIGS. 11 and 12 the resilient elongated sealing means 82 has a cross-section in the form of a truncated cone. There is a central opening or slit 83 which is matched up with the top slot of the sample unit 12 as illustrated in FIG. 9. The interior of the gasket 82 as best shown in FIG. 12 is of a rectangular configuration having the sidewalls 84, 85 and end walls 87 and 88. Within this configuration and circumscribing it are a pair of effective O-rings 89 and 91. When the gasket 82 is stretched over the pair of plates 23a, 23b the O-rings help to form a seal between the gasket and the pair of glass plates of sample unit 12. (See FIG. 9) The O-rings are not shown in FIG. 9 for simplicity and since they would be effectively compressed.

Gasket 82 is mated with a wedge shaped or truncated conical sleeve 92 (FIG. 9) which extends downwardly from the bottom of the upper buffer container 81. Moreover it is centered on the aperture 93 in such chamber. In this manner the top slot of a sample unit 12' and the polymerized gel therein may communicate both from a liquid and electrical standpoint with the upper buffer solution which is later placed in container 81. Container 81 also contains a second truncated conical sleeve 94 for receiving the second sample unit 13'. There also is an aperture 96.

Sample unit 12' is as apparent somewhat modified from the sample unit 12, for example as illustrated in FIGS. 2 and 3, in that the glass plates 23a and 23b must project above guide member 61' to allow gasket 82 to be stretched around the end of a pair of glass plates. Thus in practice, the top of the guides 61' would be shortened.

Another difference between the structure of FIG. 9 and that of FIG. 7 is that in view of the self-locating nature of the conical gasket 82 as it is wedged into the mating sleeve 92 there need be no channel corresponding to channel 71' of FIG. 7. Rather there are merely tabs 97 four of which extend from the upper buffer chamber container 81 and which accept the camming units 72' in their apertures 98. Such units 72' are shown as installed in FIG. 10. When these units are rotated and mated with the horizontal channels in the guide 61' in the same manner as in the previous embodiments, the upper buffer container 81 is locked to the sample unit 12' as illustrated in FIGS. 9 and 10 and also a sample unit 13'.

Thus an improved vertical gel slab electrophoresis apparatus and method therefor has been provided.

What is claimed is:

1. Vertical gel slab electrophoresis apparatus comprising: a pair of sample units each including a pair of clamped together spaced plates for containing gel and with open top and bottom slots; casting stand means for holding said pair of sample units vertical and for sealing said bottom slots to prevent leakage of said gel; upper buffer solution container means having a pair of apertures sealed against and mated with said top slots of said sample units to provide liquid communication with an upper buffer solution, and including means for sealing said top slots and for retaining said sample units with said upper container, whereby said casting stand may be removed from said sample units after said gel is polymerized.

2. Apparatus as in claim 1 including longitudinal resilient sealing means interposed between said sample units and said upper buffer solution container.

3. Apparatus as in claim 2 where said upper buffer container includes a pair of truncated conical elongated sleeves centered on said apertures and extending downwardly therefrom; said longitudinal resilient sealing means having a truncated conical cross-section and being stretched over said plates and top slots and mating with said sleeves to provide a liquid seal.

4. Apparatus as in claim 3 where the interior of said sealing means includes at least one effective O-ring for sealing against said pair of plates.

5. Apparatus as in claim 4 where the interior of said gasket includes at least one effective O-ring for sealing against said pair of plates.

6. A vertical gel slab electrophoresis method using a pair of sample units each including a pair of clamped together spaced plates for containing gel and with open top and bottom slots and including a casting stand for holding said units vertical, and an upper buffer solution container having a pair of apertures, said method comprising the following steps: locking said sample units in said stand in a vertical position to seal said bottom slots to prevent leakage of gel; filling at least one sample unit with gel and polymerizing; locking said upper buffer solution container to said sample units and sealing said upper slots against said apertures to provide liquid communication with an upper buffer solution; and unlocking and removing said casting stand-container combination from said sample units whereby electrophoresis may be accomplished.

7. A method as in claim 6 including the step of uniformly cooling said gel during polymerization.

8. Vertical gel slab electrophoresis apparatus comprising: an upper buffer container including at least one elongated aperture with a truncated conical sleeve centered thereon and extending downwardly therefrom; a sample unit including a pair of clamped together spaced plates for containing gel and with open top and bottom slots; an elongated resilient gasket having a truncated conical cross-section mating with said sleeve and being stretched over said pair of plates and said top slot; and means for wedging said gasket into said sleeve to provide a liquid seal.

* * * * *